(12) United States Patent
Tate

(10) Patent No.: US 7,769,109 B2
(45) Date of Patent: Aug. 3, 2010

(54) METHOD AND APPARATUS TO PERFORM MODULATION USING INTEGER TIMING RELATIONSHIPS BETWEEN INTRA SYMBOL MODULATION COMPONENTS

(75) Inventor: Larry R. Tate, Hopkinton, MA (US)

(73) Assignee: Intel Corporation, Santa Clara, CA (US)

( * ) Notice: Subject to any disclaimer, the term of this patent is extended or adjusted under 35 U.S.C. 154(b) by 2 days.

(21) Appl. No.: 12/247,965

(22) Filed: Oct. 8, 2008

(65) Prior Publication Data

US 2009/0034590 A1    Feb. 5, 2009

Related U.S. Application Data

(62) Division of application No. 10/813,143, filed on Mar. 30, 2004, now Pat. No. 7,480,330.

(51) Int. Cl.
*H04L 27/06* (2006.01)
*H03K 9/00* (2006.01)

(52) U.S. Cl. .................................... 375/316; 375/340

(58) Field of Classification Search ............... None
See application file for complete search history.

(56) References Cited

U.S. PATENT DOCUMENTS

| 6,009,488 | A | 12/1999 | Kavipurapu |
| 6,697,420 | B1 | 2/2004 | Simon et al. |
| 7,075,996 | B2 | 7/2006 | Simon et al. |
| 2005/0025252 | A1 | 2/2005 | Tate et al. |
| 2005/0068885 | A1 | 3/2005 | Becker et al. |

OTHER PUBLICATIONS

Tate, Larry R., Non-Final Office Action dated Mar. 26, 2008, filed Mar. 30, 2004, 8 pgs.

*Primary Examiner*—Tesfaldet Bocure
(74) *Attorney, Agent, or Firm*—Blakely, Sokoloff, Taylor & Zafman LLP

(57) ABSTRACT

A method and apparatus to improve modulation efficiency for chip to chip interconnects. Modulation objects that are integer multiples of a fundamental time unit (FTU) are used to populate a symbol period that is also an integer multiple of the FTU. A possible symbol set is established as the set in which the modulation object occupies every possible combination of slots within the symbol period. By permitting the modulation object to overlap positions in different symbols of the set, greater modulation efficiency is achieved.

13 Claims, 22 Drawing Sheets

FIG. 1

**FTU=s, T=3*FTU, B=2, S=12, FTU=120 Picosecond Modulation Example**

| # edges | Symbols | # of t's | # of p's | # p states | total states | Comments |
|---|---|---|---|---|---|---|
| 0 edge | φ φ φ φ φ φ φ φ φ φ φ φ | φ | φ | φ | φ | Don't use this state |
| 1 edge | p t s s s s s s s s s s | 1 | 9 | 10 | 20 | |
| 2 edge | p p s s s s s s s s s s | 2 | 6 | 7 | 28 | |
| 2 edge | p p t s s s s s s s s s | 2 | 5 | 6 | 24 | |
| 2 edge | p p p s s s s s s s s s | 2 | 4 | 5 | 20 | |
| 2 edge | p p p t s s s s s s s s | 2 | 3 | 4 | 16 | |
| 2 edge | p p p p s s s s s s s s | 2 | 2 | 3 | 12 | |
| 2 edge | p p p p t s s s s s s s | 2 | 1 | 2 | 8 | |
| 2 edge | p p p p p s s s s s s s | 2 | 0 | 1 | 4 | |
| 3 edge | p p s p s s s s s s s s | 3 | 3 | 4 | 32 | |
| 3 edge | p p s p t s s s s s s s | 3 | 2 | 3 | 24 | |
| 3 edge | p p s p p s s s s s s s | 3 | 1 | 2 | 16 | |
| 3 edge | p p s p p t s s s s s s | 3 | 0 | 1 | 8 | |
| 3 edge | p p p s p s s s s s s s | 3 | 2 | 3 | 24 | |
| 3 edge | p p p s p t s s s s s s | 3 | 1 | 2 | 16 | |
| 3 edge | p p p s p p s s s s s s | 3 | 0 | 1 | 8 | |
| 3 edge | p p p p s p s s s s s s | 3 | 1 | 2 | 16 | |
| 3 edge | p p p p s p t s s s s s | 3 | 0 | 1 | 8 | |
| 3 edge | p p p p p s p s s s s s | 3 | 0 | 1 | 8 | |
| 4 edge | p p p s p s p s s s s s | 4 | 0 | 1 | 16 | "Binary" |
| | | | | 59 | 308 | |

Total p states       59
Total States        308
Total mod     8.266786541
Total trunc mod       8

1 Edge P States
2 Edge P States
3 Edge P States
4 Edge P States

| | |
|---|---|
| columns | 10 |
| frequency | 28 |
| Payload | 20 |
| Payload Ratio | 1 |

Payload Ratio versus "binary"

FTU=s, T1=4*FTU, T2=5*FTU, B1=2, B2=2, S=16, FTU=120 Picosecond Modulation Example

| Clock: | t1 | s | s | s | s | t1 | s | s | s | s | t1 | s | s | s | s | t1 | s |
|---|---|---|---|---|---|---|---|---|---|---|---|---|---|---|---|---|---|
| ClkEdge#: | 1 | | | | | 2 | | | | | 3 | | | | | 4 | |
| Slot#: | 1 | 2 | 3 | 4 | 5 | 6 | 7 | 8 | 9 | 10 | 11 | 12 | 13 | 14 | 15 | 16 | |
| Clock Assignment: | 1 | 1 | 1 | 1 | 2 | 2 | 2 | 2 | 3 | 3 | 3 | 3 | 4 | 4 | 4 | 4 | |

| # edges | Symbols (Slot 1–16) | # of t1's | # of t2's | #p1's | p1' states | #p2's | p2' states | p states | B1 | B2 | total states |
|---|---|---|---|---|---|---|---|---|---|---|---|
| 1 T1 | p1 p1 p1 p1 s s s s s s s s s s s s | 1 | 0 | 12 | 13 | 0 | 1 | 14 | 2 | 2 | 26 |
| 2 T1 | p1 p1 p1 p1 s s s s p1 p1 p1 p1 s s s s | 2 | 0 | 8 | 9 | 0 | 1 | 10 | 2 | 2 | 36 |
| 2 T1 | p1 p1 p1 p1 s s s t1 s s s s p1 p1 p1 s | 2 | 0 | 7 | 8 | 0 | 1 | 9 | 2 | 2 | 32 |
| 2 T1 | p1 p1 p1 p1 s s t1 s s s s s s p1 p1 p1 | 2 | 0 | 7 | 8 | 0 | 1 | 9 | 2 | 2 | 32 |
| 2 T1 | p1 p1 p1 p1 s t1 s s s s s s s s p1 p1 | 2 | 0 | 6 | 7 | 0 | 1 | 8 | 2 | 2 | 28 |
| 2 T1 | p1 p1 p1 s t1 s s s s s s s s s p1 p1 | 2 | 0 | 5 | 6 | 0 | 1 | 7 | 2 | 2 | 24 |
| 2 T1 | p1 p1 s t1 s s s s s s s s s s p1 p1 | 2 | 0 | 4 | 5 | 0 | 1 | 6 | 2 | 2 | 20 |
| 2 T1 | p1 s t1 s s s s s s s s s s s p1 p1 | 2 | 0 | 3 | 4 | 0 | 1 | 5 | 2 | 2 | 16 |
| 2 T1 | s t1 s s s s s s s s s s s s p1 p1 | 2 | 0 | 2 | 3 | 0 | 1 | 4 | 2 | 2 | 12 |
| 2 T1 | t1 s s s s s s s s s s s s s p1 p1 | 2 | 0 | 1 | 2 | 0 | 1 | 3 | 2 | 2 | 8 |
| 2 T1 | s s s s s s s s s s s s s s t1 s | 2 | 0 | 0 | 1 | 0 | 1 | 2 | 2 | 2 | 4 |
| 3 T1 | p1 p1 p1 p1 s s s s p1 p1 p1 p1 s s s s | 3 | 0 | 4 | 5 | 0 | 1 | 6 | 2 | 2 | 40 |
| 3 T1 | p1 p1 p1 p1 s s s t1 s s s s p1 p1 p1 s | 3 | 0 | 3 | 4 | 0 | 1 | 5 | 2 | 2 | 32 |
| 3 T1 | p1 p1 p1 p1 s s t1 s s s s s s p1 p1 p1 | 3 | 0 | 3 | 4 | 0 | 1 | 5 | 2 | 2 | 32 |
| 3 T1 | p1 p1 p1 p1 s t1 s s s s s s s s p1 p1 | 3 | 0 | 2 | 3 | 0 | 1 | 4 | 2 | 2 | 24 |
| 3 T1 | p1 p1 p1 s t1 s s s s s s s s s p1 p1 | 3 | 0 | 2 | 3 | 0 | 1 | 4 | 2 | 2 | 24 |
| 3 T1 | p1 p1 s t1 s s s s s s s s s s p1 p1 | 3 | 0 | 1 | 2 | 0 | 1 | 3 | 2 | 2 | 16 |
| 3 T1 | p1 s t1 s s s s s s s s s s s p1 p1 | 3 | 0 | 0 | 1 | 0 | 1 | 2 | 2 | 2 | 8 |
| 3 T1 | s s s s s s s s p1 p1 p1 p1 s s s s | 3 | 0 | 3 | 4 | 0 | 1 | 5 | 2 | 2 | 32 |
| 3 T1 | s s s s s s s t1 s s s s p1 p1 p1 s | 3 | 0 | 2 | 3 | 0 | 1 | 4 | 2 | 2 | 24 |
| 3 T1 | s s s s s s t1 s s s s s s p1 p1 p1 | 3 | 0 | 2 | 3 | 0 | 1 | 4 | 2 | 2 | 24 |
| 3 T1 | s s s s s t1 s s s s s s s s p1 p1 | 3 | 0 | 1 | 2 | 0 | 1 | 3 | 2 | 2 | 16 |
| 3 T1 | s s s s t1 s s s s s s s s s p1 p1 | 3 | 0 | 0 | 1 | 0 | 1 | 2 | 2 | 2 | 8 |
| 3 T1 | s s s s s s s s s s s s p1 p1 p1 s | 3 | 0 | 2 | 3 | 0 | 1 | 4 | 2 | 2 | 24 |
| 3 T1 | s s s s s s s s s s s s s p1 p1 p1 | 3 | 0 | 2 | 3 | 0 | 1 | 4 | 2 | 2 | 16 |
| 3 T1 | s s s s s s s s s s s s s s p1 p1 | 3 | 0 | 1 | 2 | 0 | 1 | 3 | 2 | 2 | 8 |
| 3 T1 | s s s s s s s s s s s s s s s t1 | 3 | 0 | 0 | 1 | 0 | 1 | 2 | 2 | 2 | 8 |

METHOD AND APPARATUS TO PERFORM MODULATION USING INTEGER TIMING RELATIONSHIPS BETWEEN INTRA SYMBOL MODULATION COMPONENTS

This patent application is a divisional of application Ser. No. 10/813,143, filed Mar. 30, 2004 now U.S. Pat. No. 7,480,330, entitled, METHOD AND APPARATUS TO PERFORM MODULATION USING INTEGER TIMING RELATIONSHIPS BETWEEN INTRA SYMBOL MODULATION COMPONENTS.

BACKGROUND

1. Field of the Invention

Embodiments of the invention relate to modulation. More specifically, embodiments of the invention relate to an improved encoding density modulation scheme.

2. Description of the Related Art

Various forms of modulation have long been used to encode data with greater efficiency so that more data can be transmitted during a particular time period over a transmission medium. Combinations of various modulation techniques such as, pulse width modulation, amplitude modulation and rise time modulation have been employed to improve the encoding density of modulation schemes. See for example, application entitled "Symbol-Based Signaling For An Electromagnetically-Coupled Bus System," Ser. No. 09/714,244, now U.S. Pat. No. 6,697,420. However, such schemes typically employ a fixed base pulse residing in a fixed location within the symbol period. This can have a significant limiting effect on the possible modulation symbols available and therefore the modulation gain achievable.

BRIEF DESCRIPTION OF THE DRAWINGS

Embodiments of the invention are illustrated by way of example and not by way of limitation in the figures of the accompanying drawings in which like references indicate similar elements. It should be noted that different references to "an" or "one" embodiment in this disclosure are not necessarily to the same embodiment, and such references mean at least one.

FIG. 1 is a spreadsheet of a symbol set according to one embodiment of the invention.

FIG. 2 is a spreadsheet showing piecewise linear (PWL) depictions of some symbols according to one embodiment of the invention.

DETAILED DESCRIPTION

Figure 3:
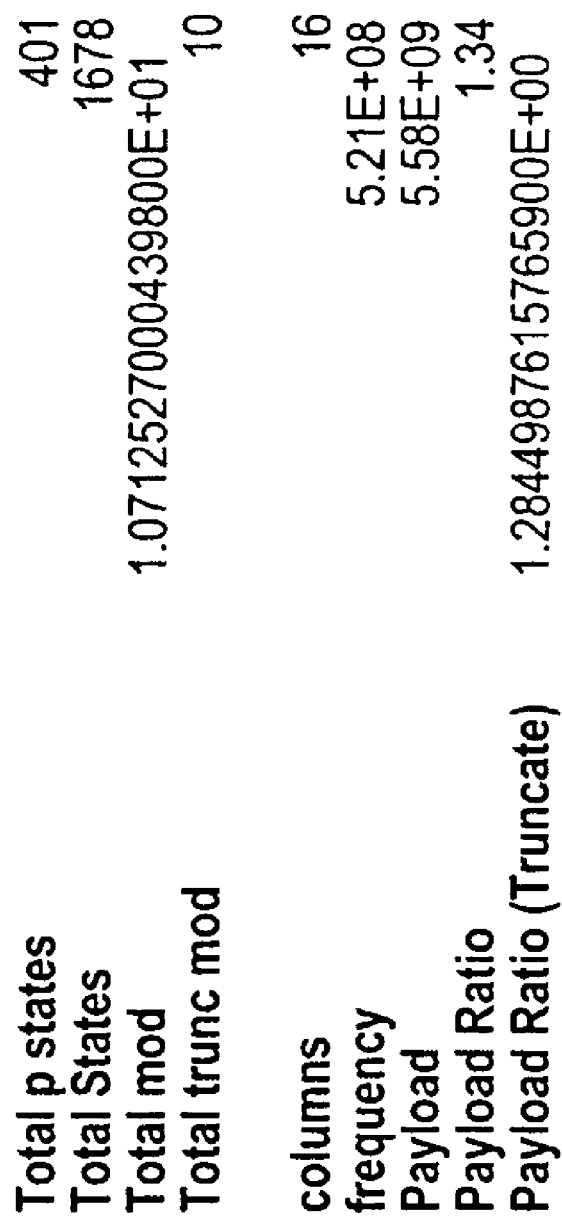
FIG. 3 is a spreadsheet of symbols having the same parameters as used for the symbols of FIG. 2.

One embodiment of the invention provides an improved modulation technique premised on multiples of a fundamental unit of time (FTU). Selection of the FTU size may be based on the minimum phase slot size for the system. In equalized channels, jitter and other noise factors over manufacturing variations become the limiting factor on slot size that can be resolved for a given bit error rate (BER). In this scheme, data is encoded in symbols in relation to the timing relationship of modulation objects within the symbol. In an embodiment, a symbol period ("S") is an integer ("N") multiple of the FTU. The symbol period may be selected in accordance with latency, complexity, and timing resolution possible with the timing constraints in the system employed. The delay lock loops (DLL), phase lock loops (PLL), delay elements, process employed, design of RF channel, manufacturing variations, and feature size all effect the desired symbol period.

In this description a phase slot for phase modulation within the symbol period is abbreviated as "s." The examples below have s=1 FTU, in some embodiments, variable phase slots may be constructed from any integer multiple of the FTU, where the FTU in this case must equal or exceed the minimum time increment resolvable in the semiconductor process. The time during which single transition in amplitude may occur between edges plus the minimum time space during which a new edge transition is not permitted in a communication channel to control intersymbol interference (ISI) is abbreviated as $T_i$. The set of $T_i$ $\{T_i\}$ for i=1, 2, ... n is defined as the set of different widths required for general edge rate and amplitude modulation that include the ISI spacer. The $T_i$ for each member of the set is an integer multiple of the FTU. In one embodiment, the integer multiple and other modulation parameters are chosen based on optimizing the bit error rate (BER) performance in an ISI communication channel in tandem with optimizing the channel equalization.

In chip to chip interconnect signaling, the amplitude is frequently permitted to have two (binary), three pulse-amplitude modulation (3 PAM) or four pulse amplitude modulation (4 PAM) possible levels. For the case of three amplitude levels, ground, $V_{dd}$ and $V_{ref}(V_{dd}/2)$ are reasonable implementation choices. With three possible amplitude levels, two transitions are possible at each edge. This permits one bit of amplitude modulation to be encoded per edge. It is of course contemplated that in addition to amplitude modulation, rise time modulation is supported by the modulation scheme described below. Moreover, other embodiments may use an arbitrary number of amplitude levels and/or rise times. The number of possible transitions per edge is abbreviated as "B" in this description. Thus, for three amplitude levels, B=2. The total symbol set for a set of parameters $\{T_i\}$, B and S is formed by choosing all combinations of the set $\{T_i\}$ that fit within S. Symbol mapping logic may be used to select a subset of total available symbols based on the ISI and the other properties of symbols including the symbols needed to form an integer modulation factor across the small number of input/output (I/O) pads. Stated differently, since as discussed below, the modulation is log base two of the total number of states, some symbols may be unused because the log base two of the total status must be an integer. However, where a plurality of modulators (M) are employed, e.g. M≧2, it is possible to modulate fractional bits across plural modulators. For example, if M=2 and each modulator could modulate 4½ bit, the additional half bit can be modulated by both $M_1$ and $M_2$ to yield nine bits of total modulations.

FIG. 1 is a spreadsheet of a symbol set according to one embodiment of the invention. In this example, FTU is equal to s is equal to 120 pico seconds and T is equal to 3 FTU. Bearing in mind that T is equal to the sum of the transition region (rise time) plus the time during which no transition may occur. For this example, B is equal to 2, which implies two possible transitions from the current amplitude state which further requires a minimum of three possible amplitude levels. S is equal to 12 FTU and each column equals one FTU. Thus, in this example, the symbol period is equal to twelve phase slots. All the possible symbols may be derived by placing the modulation object T in all the possible places it may occur within the symbol. For this 3 FTU "T" example, the modulation object T is defined as tss (where t signifies a transition which may in theory occupy any fraction of the 3 phase slot wide "T".) in consecutive cells along a row in a spreadsheet. "p" notation serves as a wildcard to represent multiple "T" as follows: the sequence of one or more p's may be paired with one t. This is defined to be equivalent to all possible combinations of t substituted for the p's one at a time with the remaining p's replaced by s'. For example, pppt is equal to (ssst, ssts, stss and tsss) and tppp is equal to pppt.

Figure 2:
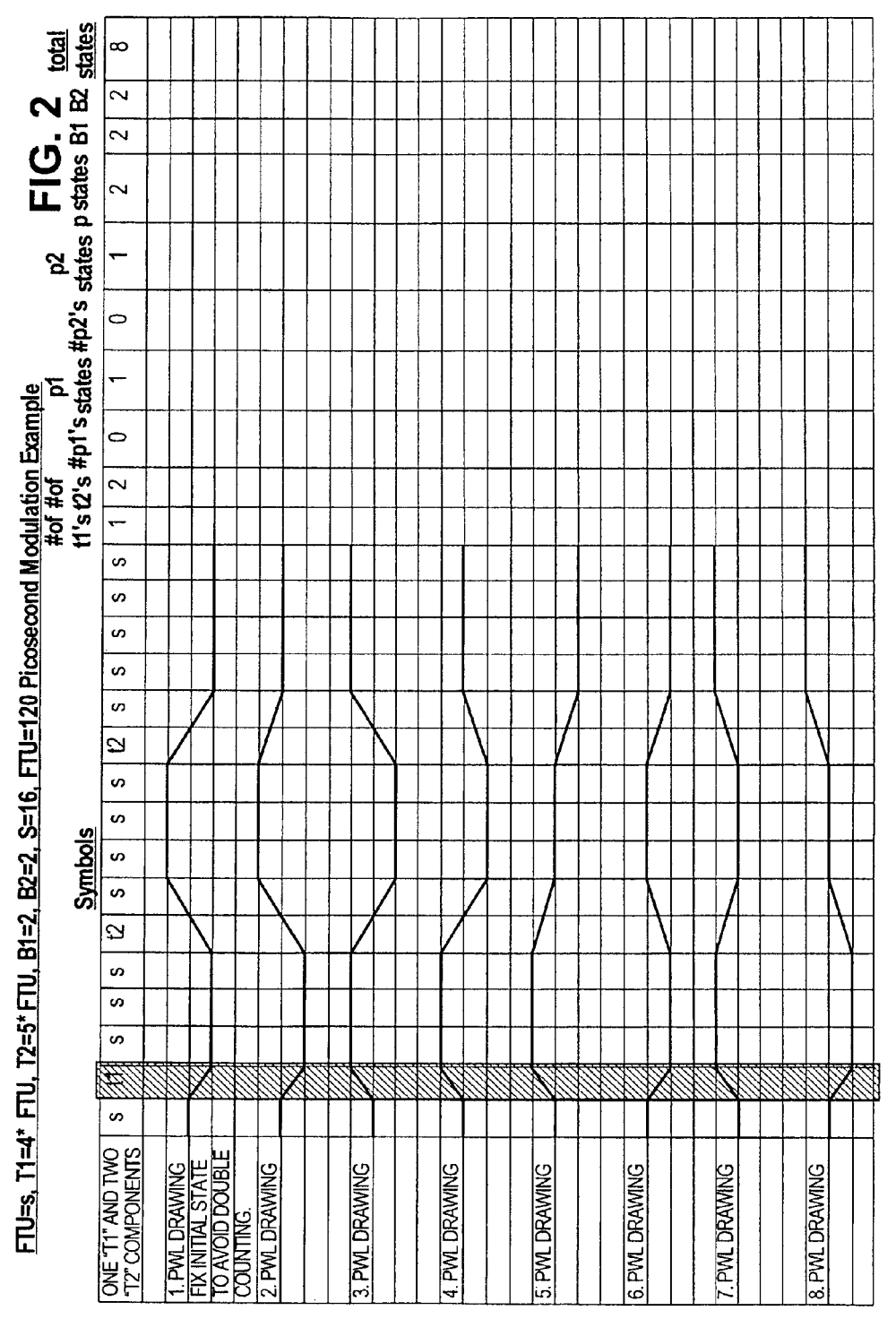

The first row of the spreadsheet shows the symbol in which no transitions occur. In one embodiment of the invention, this state is unused. As can to be seen in the spreadsheet of FIG. 1, 0 to 4 edge transitions are possible within the symbol period. This is found by dividing S by T. The column headed number of t's indicates the number of transitions within the symbol. The number of p's indicates the number of wild cards for t present in the symbol. The number of p states is equal to the number of p's plus 1. The number of total states for row is given by B raised to the power of the number of transitions (t's) times the number of p states. For example, for the second row, $B^1 \times 10 = 2^1 \times 10 = 20$. Similarly, for the third row, $B^2 \times 7 = 4 \times 7 = 28$ and so forth. This large number of states is in part a result of permitting the modulation objects to overlap the positions of other modulation objects within different symbols. Stated differently, because the modulation object can occupy any position within a symbol period, except slots occupied by other modulation objects of the same symbol, higher modulation efficiency is achieved.

The total number of states for all rows aggregated less the unused state reflected in the first row is 308 total states. The total modulation is given by log base two of the total states. Since the input to a set of modulators must be an integer, effective modulation is truncated to 8. Thus, for this example, there would be a number of unused symbols from the possible symbol set. While it is possible for any set of T, B, and S to graphically represent the possible symbol set and do a spreadsheet calculation, this is inefficient timing consuming and error prone. The following close form solution yields the total states for symbols formed from a single modulation object and was mathematically derived from the above counting rules.

$$\text{Total states } (T_1) = \sum_{n=1}^{Fix(S/T)} B^n \sum_{m=1}^{n} C(n,m) * (S - n*T + 1)^m$$

Where C(n,m) is a two dimensional matrix of coefficients that was derived from the coefficients for integer sums of the respective powers as follows: first, note that the integer sum for "i" from zero to "n" to the "p" power, $$\sum_{i=0}^{n} i^p,$$

may be expressed as a polynomial of order "p+1". The coefficients for these integer sum polynomials may be found in the literature. Next, counting rules were developed corresponding to the notation employed in counting the symbols in the spreadsheet examples of FIG. 1 and FIG. 3. Finally, the resulting counting formulas contain nested sums of the form:

$$\sum_{i=0}^{x} \left( \sum_{j=0}^{i} \left( \sum_{k=0}^{j} \cdots \sum_{z=0}^{y} z \right) \right).$$

These nested loops were unfolded to form a polynomial of order equal to the maximum number of edges in a modulated symbol with resulting C(n,m) coefficients. "n" corresponds to the number of transitions that are being counted by the inner loop; "m" sums the polynomial for a fixed number of transitions. The argument of the polynomial, (S−n*T+1), reflects the number of slots remaining after subtracting the slots required to fit "n" transitions. Finally, it should be noted that the sum of C(n,m) coefficients must be equal to one for any given polynomial.

Phase and amplitude modulation are modeled in this equation, in which B is the number of transitions possible at an edge. Thus, B becomes the base for the exponential relationship per edge for the sum of amplitude and rise time modulation. For example, for two possible state transitions, B=2. The outer summation computes the amplitude state multiplier for the number of edges "n" from 1 (zero case not used) to the maximum number "fix(S/T)" of edges that will fit in the symbol. The amplitude state multiplier is then multiplied by the total number of phase states associated with "n" edges as computed by the inner summation to form the total number of states. This closed form solution allows optimization of parameters for systems using a single type of modulation object.

FIG. 2 is a spreadsheet showing piecewise linear (PWL) depictions of some symbols according to one embodiment of the invention. In a depicted example, the set $\{T_1\}=\{T_1, T_2\}$ (i.e., rise time modulation objects may be used to form the symbols). Again in this example, the phase slot size s=1 FTU. For drawing convenience, the rise time of $T_1$ is drawn as 1 FTU and the rise time of $T_2$ is drawn as 2 FTU. In other embodiments, modulation objects may have other resolvable rise time values. The modulation in the drawing depicts three amplitude levels. To avoid double counting, each symbol starts at $V_{dd}/2$ amplitude. However, symbols could start at a ground or $V_{dd}$ amplitude as determined by the preceding symbol. Following the same nomenclature as FIG. 1, $T_1$=4 FTU's (shorter rise time), $T_2$=5 FTU's (longer rise time), $B_1$=2, $B_2$=2 and S=16. An FTU is again assumed to be 120 pico seconds. $T_1$ is defined as $t_1$sss and $T_2$ is defined $t_2$ssss. These symbols illustrate symbols having two kinds of modulation objects within the symbol. The total number of states for a two modulation object symbol set is given by the equation:

$$\text{Total States } (T_1 T_2) = \sum_{n_1=1}^{Fix(S/T_1)} \sum_{n_2=1}^{Fix((S-T_1)/T_2)} B_1^{n_1} B_2^{n_2}((n_1+n_2)!/(n_1!n_2!))$$

$$\sum_{m=1}^{n_1+n_2} C((n_1+n_2), m) * (S - n_1 T_1 - n_2 T_2 + 1)^m$$

Where $C((n_1+n_2),m)$ is the two dimensional matrix of coefficients for the nested collapsing sums formula that was derived from the coefficient for straight sum of powers as discussed above in relation to FIG. 1. Where "n1" corresponds to the number of "$T_1$" modulation components and "n2" corresponds to the number of "$T_2$" modulation components. "$B_1$" and "$B_2$" are the number of possible transitions per edge for "$T_1$" and "$T_2$" respectively.

The mixed term gain, the gain attributable to symbols containing two different rise times, increases the modulation efficiency in one embodiment of the invention. This close form solution permits optimization of parameters where two types of modulation objects are supported e.g., modulation objects having different rise times or occupying a different numbers of slots. This formula may be naturally extended to support any number of different sized modulation objects.

FIG. 3 is a spreadsheet of symbols having the same parameters as used for the symbols of FIG. 2. In fact, FIG. 2 corresponds to row number 58 on FIG. 3 (the 5$^{th}$ "T1T2T2" symbol row). The clocking scheme in one embodiment of the invention is depicted above the symbol columns. This spreadsheet reflects 1678 total states which is in exact agreement with two modulation object total states equation above.

Figure 4:
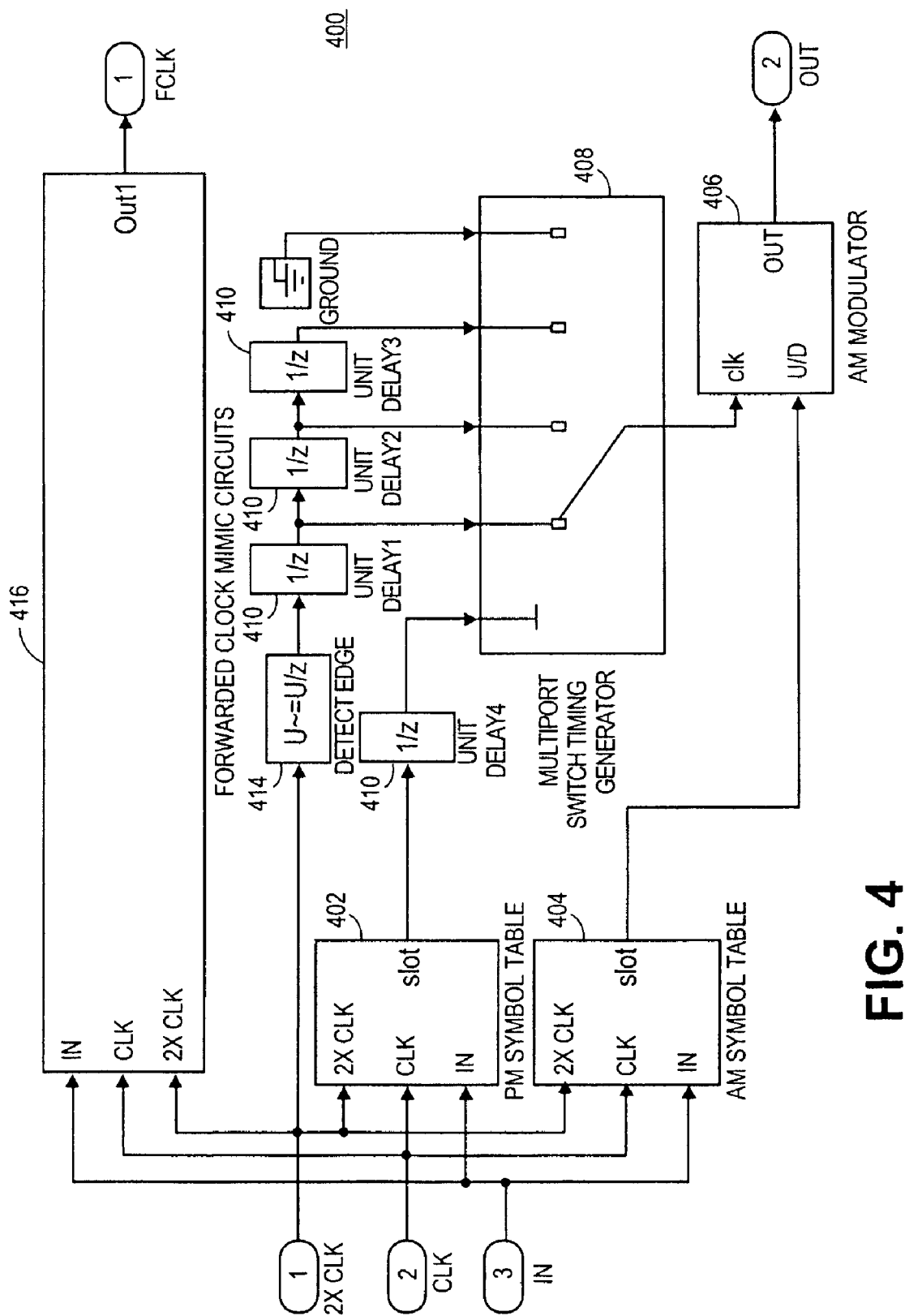
FIG. 4 is a block diagram of a modulator of one embodiment of the invention.

FIG. 4 is a block diagram of a modulator of one embodiment of the invention. Modulator 400 may implement, for example, modulation using symbols of the format depicted in FIG. 3. Modulator 400 includes phase modulation (PM) symbol table 402, and amplitude modulation (AM) symbol table 404, which map an incoming data stream to symbols such as those depicted in FIG. 3. In one embodiment, the modulator and demodulator designs have an orthogonal architecture and circuit implementations of the AM and PM. The orthogonal architecture leads to parallel paths rather than a deepening of the critical path as would be the case where the AM and PM were interdependent. Similarly, in embodiments having rise time components, the rise time modulation (RTM) may have an orthogonal architecture to the AM and PM resulting in parallel processing of this component as well. A clock labeled "2x" is supplied to an edge detection unit 414. Delay units 410 each provided a delay equal to one phase slot to permit generation of a pulse at the appropriate distance from the appropriate reference clock edges as depicted at the top of FIG. 3. The multiport switch timing generator, 408, generates control signals to insert the phase timing by a control multiplexer that selects the correct pulse for the phase modulation timing for the amplitude modulator 406. Note that sufficient delay should be provided to allow the control signals to settle before the PM timing edges pass through the multiplexer. The correct AM voltage level is determined by control signals from AM symbol table 404 in conjunction with the prior AM state information contained within AM modulator 406. This is described in more detail with reference to FIG. 4A. Both the PM symbol table 402 and the AM symbol table 404, change control signals every third slot edge group since the clock edge changes is a function of the edge input into the block, thereby efficiently implementing the entire symbol timing by repeatedly reusing the hardware for only one edge group. In one embodiment, the detailed timing within the edge groups is entirely generated by delay elements calibrated to the process using a DLL or similar technique.

Modulator 400 also includes a forwarded clock circuit 416 to mimic the delay in the remainder of the modulator and provide a forwarded clock with timing consistent with the output of the modulator. In one embodiment, the forwarded clock has the edge slot assignments shown in FIG. 3. The forwarded clock solution minimizes the effect of jitter on the transmitted signal. Alternative embodiment has no forwarded clock, but rather uses an embedded clock signal recovered at the demodulator with a clock recovery circuit. In another embodiment, a globally distributed clock may be used.

Figure 4A:
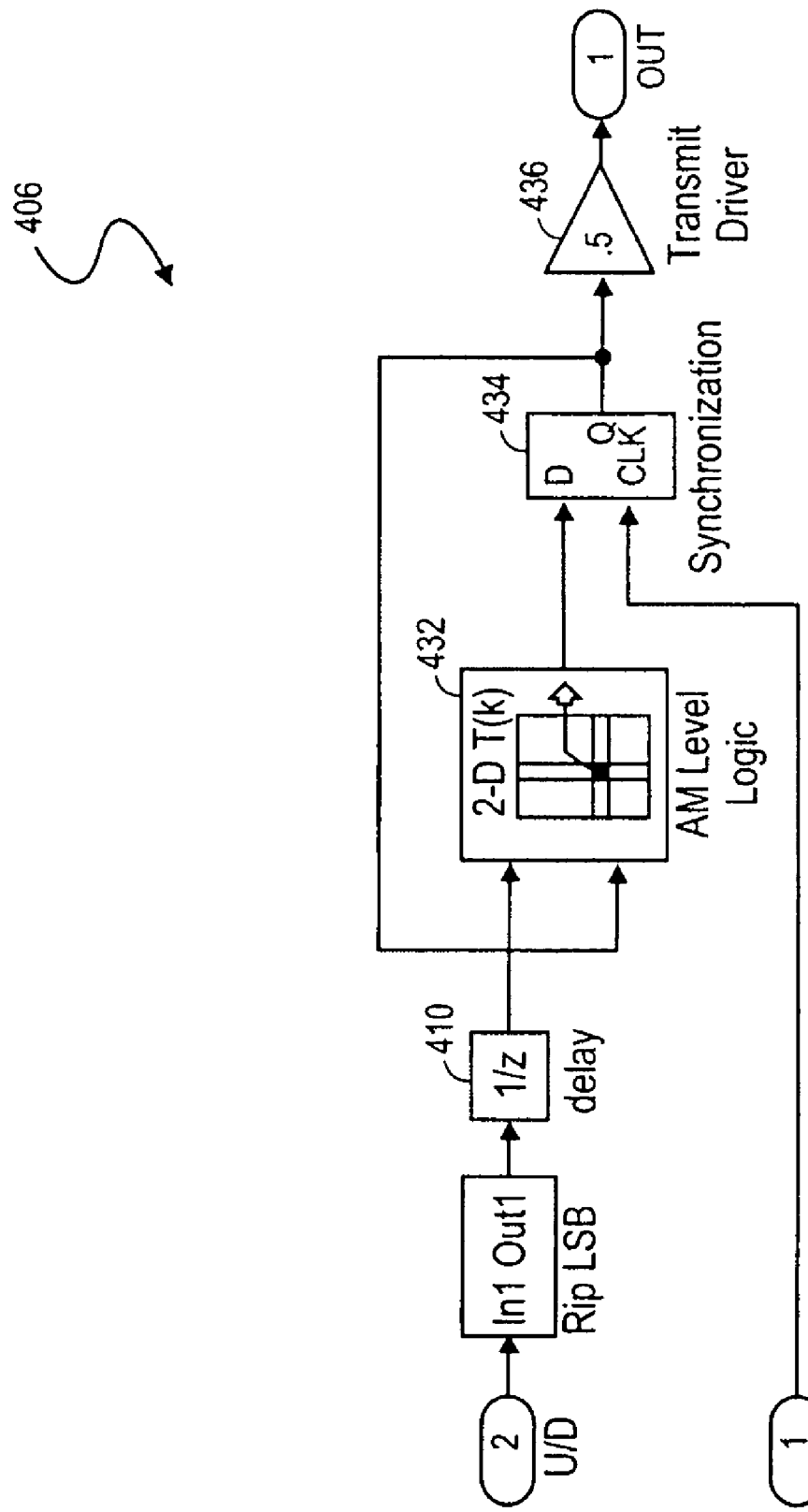
FIG. 4A is a block diagram of the AM modulator of FIG. 4.

FIG. 4A is a block diagram of the AM modulator of FIG. 4. The AM modulator 406 includes the level determination logic block 432 a synchronization unit 434, and transmit driver 436. A one slot delay 410 is introduced to maintain timing consistency with the clock symbol coming from the phase modulation portion of the modulator 400. The logic level determination unit 432 determines the AM level based on the signal from the AM symbol table and the prior state of the AM level as feedback from synchronization unit 434. The transmit driver 436 ultimately asserts the signal contingent on the symbols onto the bus with correct phase modulation and amplitude modulation.

Figure 5:
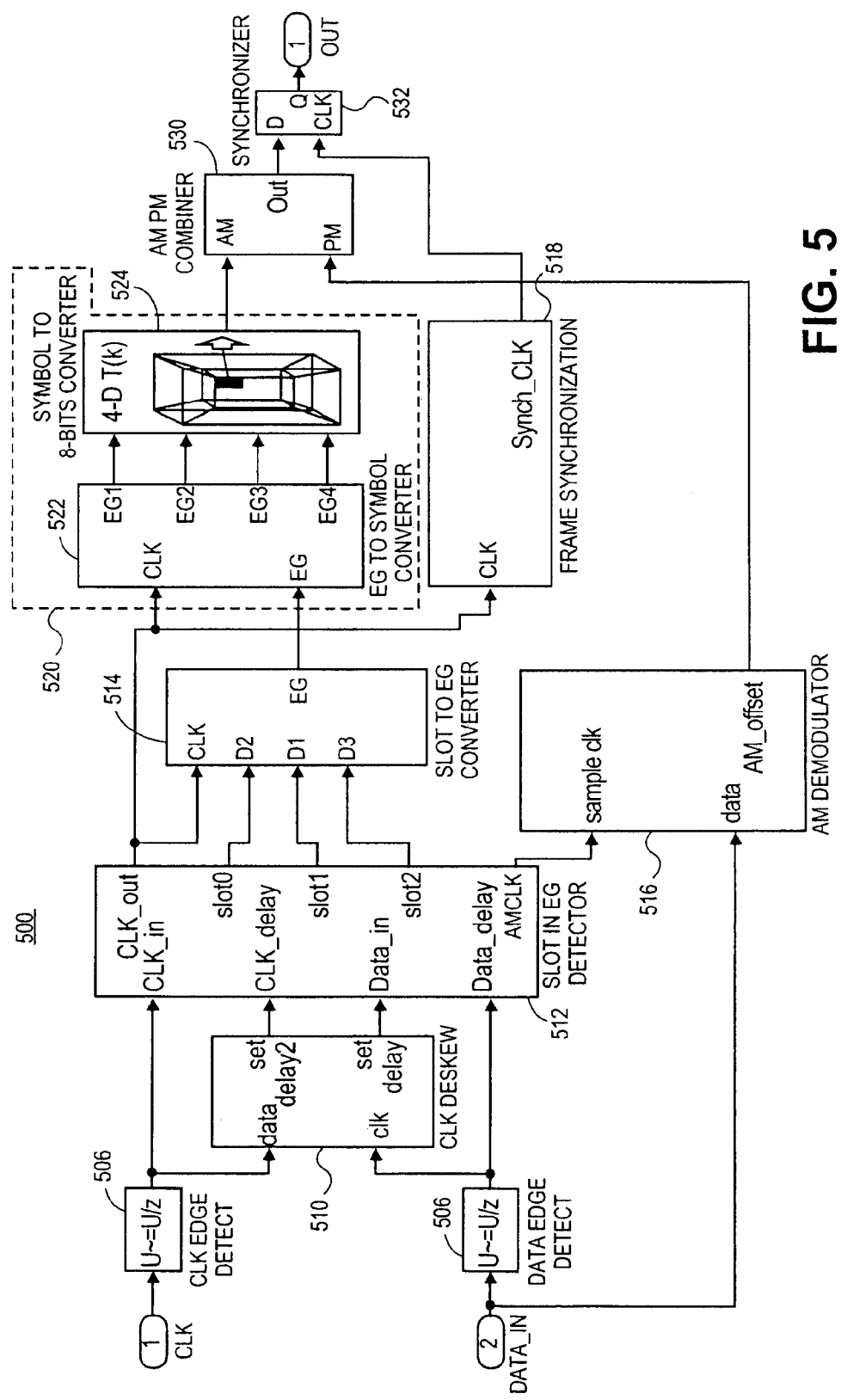
FIG. 5 is a block diagram of a demodulator of one embodiment of the invention.

FIG. 5 is a block diagram of a demodulator of one embodiment of the invention. Demodulator 500 includes a first and second edge-detect circuits 506 which receive the forwarded clock and data. In one embodiment, each edge detector 506 generates a slot sized pulse. The generated slot size pulse simplifies the remainder of the design and eliminates the need for reset circuits in the circuits downstream. The slot sized pulses are provided as an input to the clock deskew circuit 510. The output of the deskew circuit connects to the input of the slot in edge group detector 512 (described in more detail with reference to FIG. 5A below). In one embodiment, the clock deskew circuit 510 inserts delays that compensate for different routing delays between clock and data and compensates for circuit variations to individually optimize the phase and amplitude demodulation eyes. The slot in edge group detector provides the stream of per slot edge information (discussed below) to the slot to edge group converter 415. Incoming data is also fed into an AM demodulator 516 (described in more detail with reference to FIG. 5C below). The AM demodulator 516 also receives an eye strobe signal from the slot in edge group detector 512. In other possible embodiments, the eye strobe signal could be directly derived from the CLK and DATA_IN signals to further decouple the AM and PM demodulators. The slot in edge group detector 512 drives the slot to edge group converter 514 (described in more detail with reference to FIG. 5B). The slot to edge group converter 514 assembles four edge group values and indexes into a PM demapping table. The slot to edge group converter 514 provides the edge group to demapping logic 520, which includes an edge group symbol converter 522 and a symbol to 8 bits converter 524. The PM converted symbol is supplied to an AM PM combiner 530, which also receives the AM offset from AM demodulator 516. Frame synchronization unit 518 supplies the clock to the register 532 used to synchronize the output of the demodulator based on the clock from the synchronization unit 518.

Figure 5A:
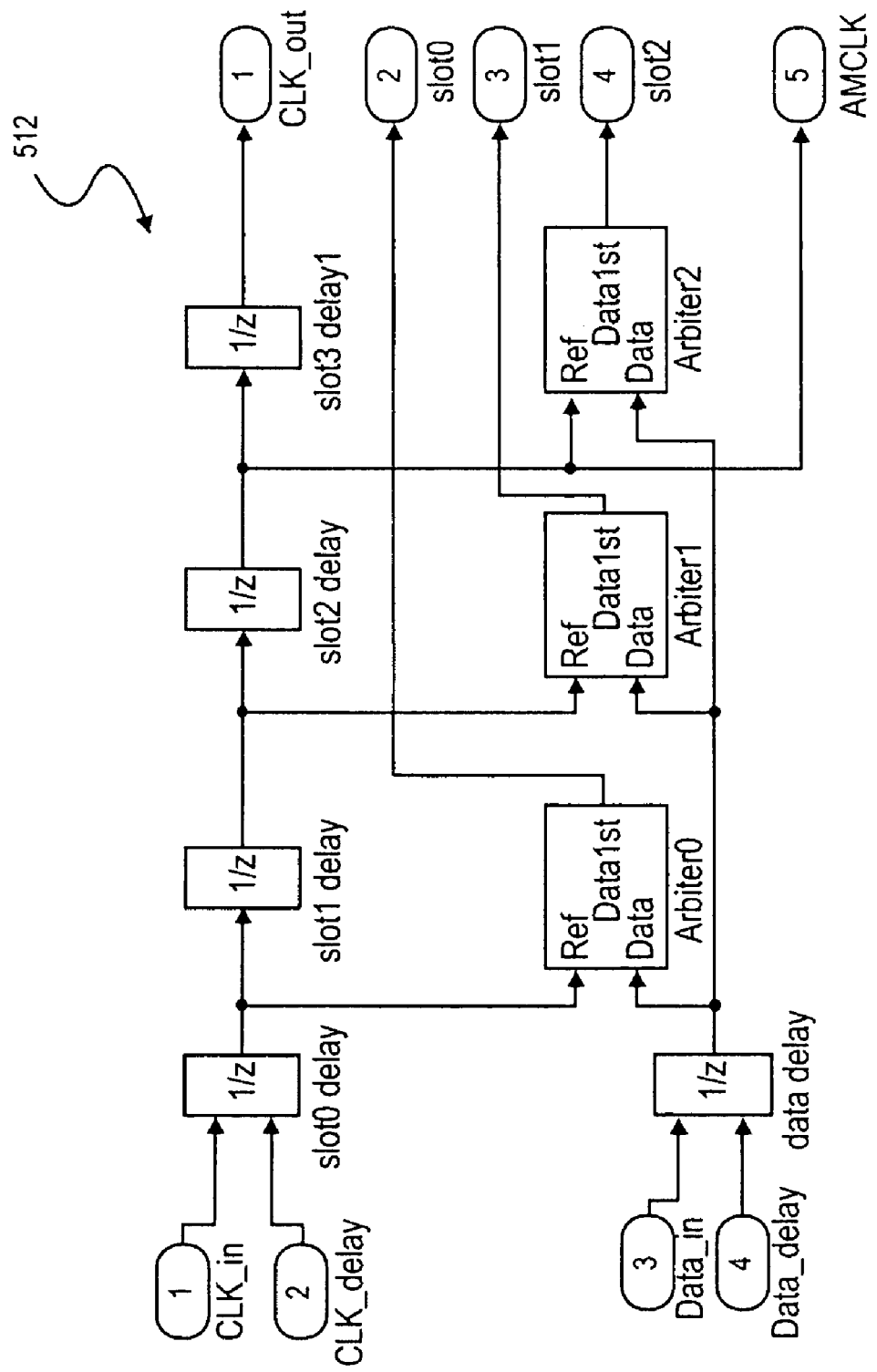
FIG. 5A is a more detailed block diagram of the slot in edge group detector of FIG. 5.

FIG. 5A is a more detailed block diagram of the slot in edge group detector of FIG. 5. The slot in edge group detector compares data pulses with appropriately slot delayed clock pulses to determine the slots in which phase changes occur. A plurality of slot delays and arbiters are used for this purpose.

The information is streamed from the slot in edge group detector 512 on a per slot basis and is then reassembled by the slot to edge group converter 514.

Figure 5B:
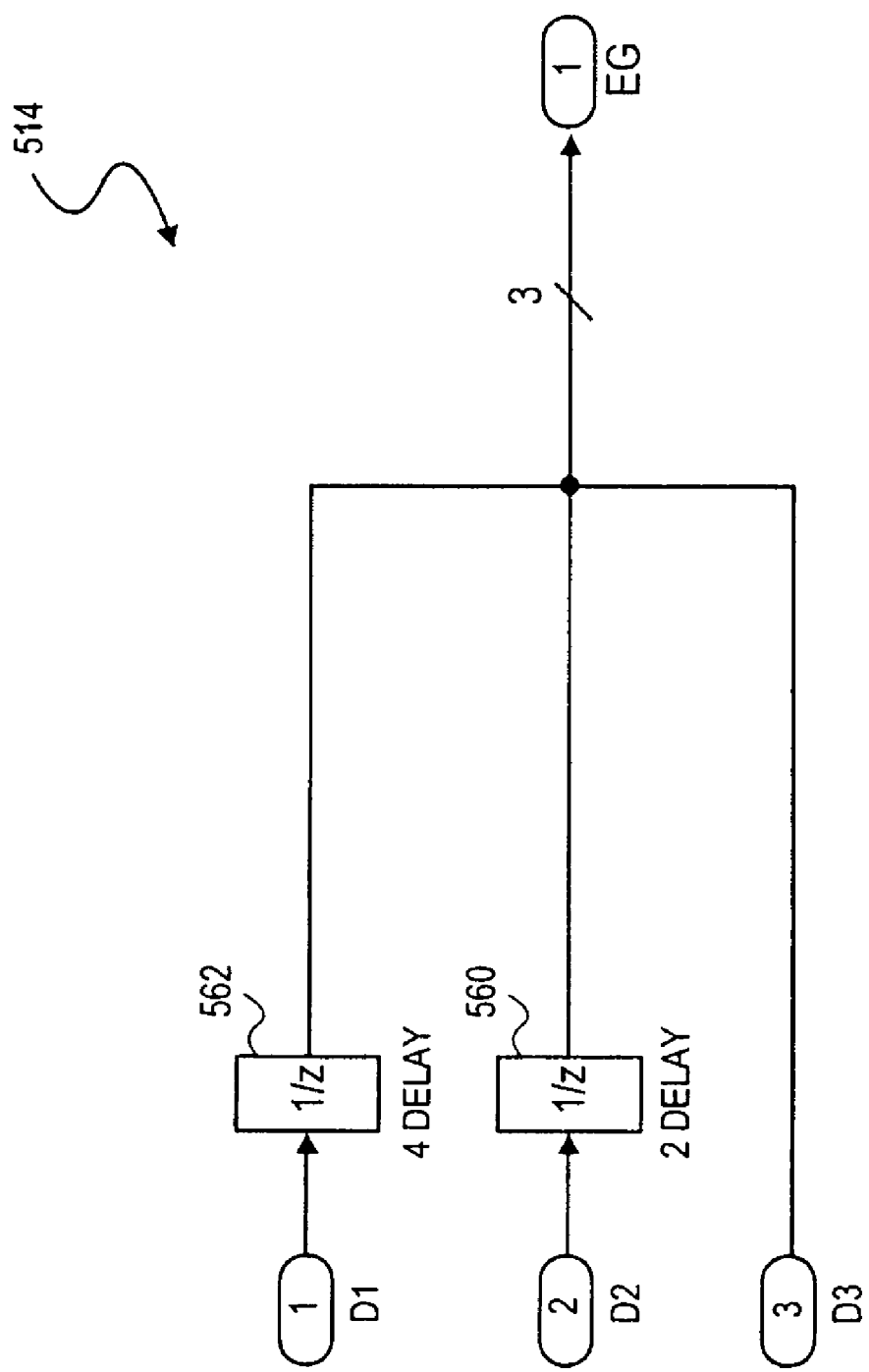
FIG. 5B shows the slot to edge group converter of FIG. 5.

FIG. 5B shows the slot to edge group converter of FIG. 5. The slot to edge group converter 514 uses delay elements 560 and 562 to time align the slot edge detection data provided by slot in edge group detector 512 to determine where within the edge group the phase transition occurred. In this example, four edge groups form a symbol. The edge group assembled by the slot to edge group converter 514 is provided to the edge group symbol converter 522 as described above in connection with FIG. 5.

Figure 5C:
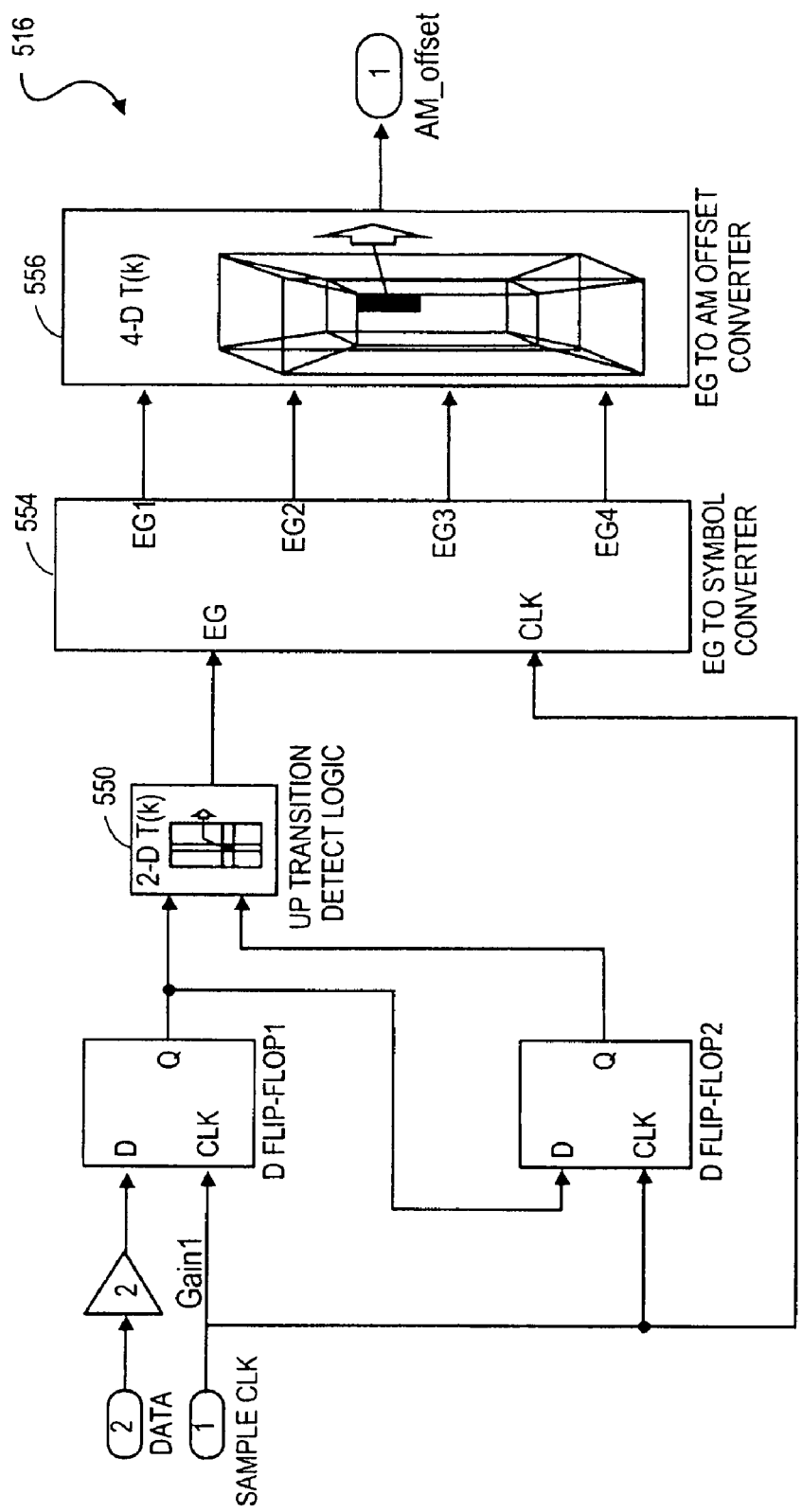
FIG. 5C is a more detailed block diagram of the AM demodulator of FIG. 5.

FIG. 5C is a more detailed block diagram of the AM demodulator of FIG. 5. The AM demodulator 516 samples the level at the end of each edge group and determines whether a change in level has occurred. Transition detect logic 550 detects these transitions. The change indexes a table to determine whether the change was up or down for this 3 AM state example. The four possible transitions per edge group are then assembled into a symbol group using the slot to edge converter described above. The edge group symbol converter 554 indexes the edge group into edge group offset converter which includes an AM symbol demapping table to determine the AM value originally set by the modulator AM symbol table of the modulator (400 of FIG. 4).

The various circuits shown block diagrammatically in FIG. 4-5C used delays, multiplexing, gates, drivers, arbitrators, and operational amplifiers. Some embodiments of the invention may employ additional multiplexing to save silicon area/cost. In one embodiment, all gates, multiplexers and control logic are implemented with near minimum sized transistors. This will result in only a nominal increase in the size of the transceiver relative to a binary transceiver.

Figure 6:
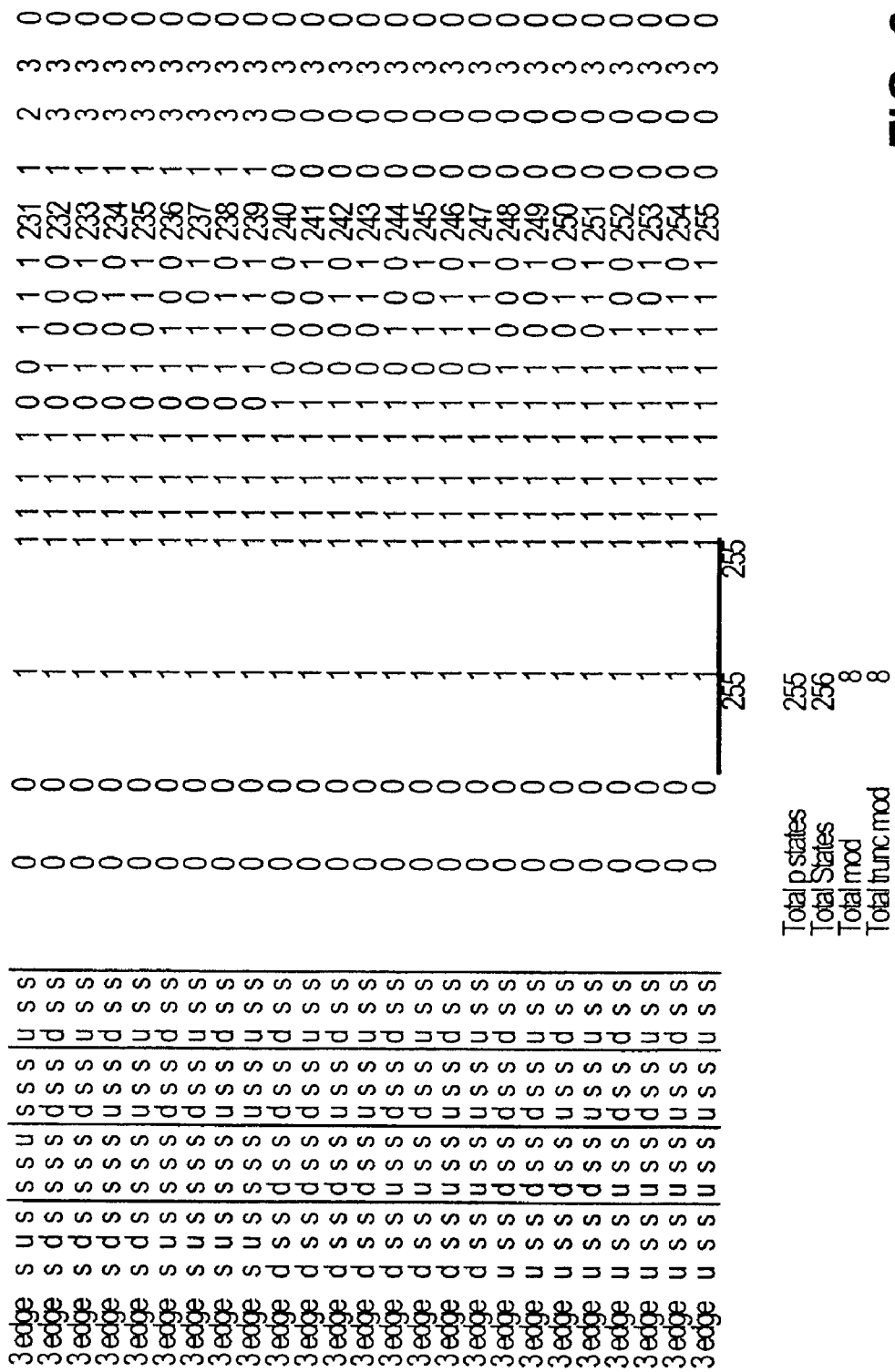
FIG. 6 is a spreadsheet showing state assignments for the embodiment of the modulator and demodulators shown in FIGS. 4 and 5.

FIG. 6 is a spreadsheet showing state assignments for one embodiment of the modulator and demodulators shown in FIGS. 4 and 5.

Figure 7:
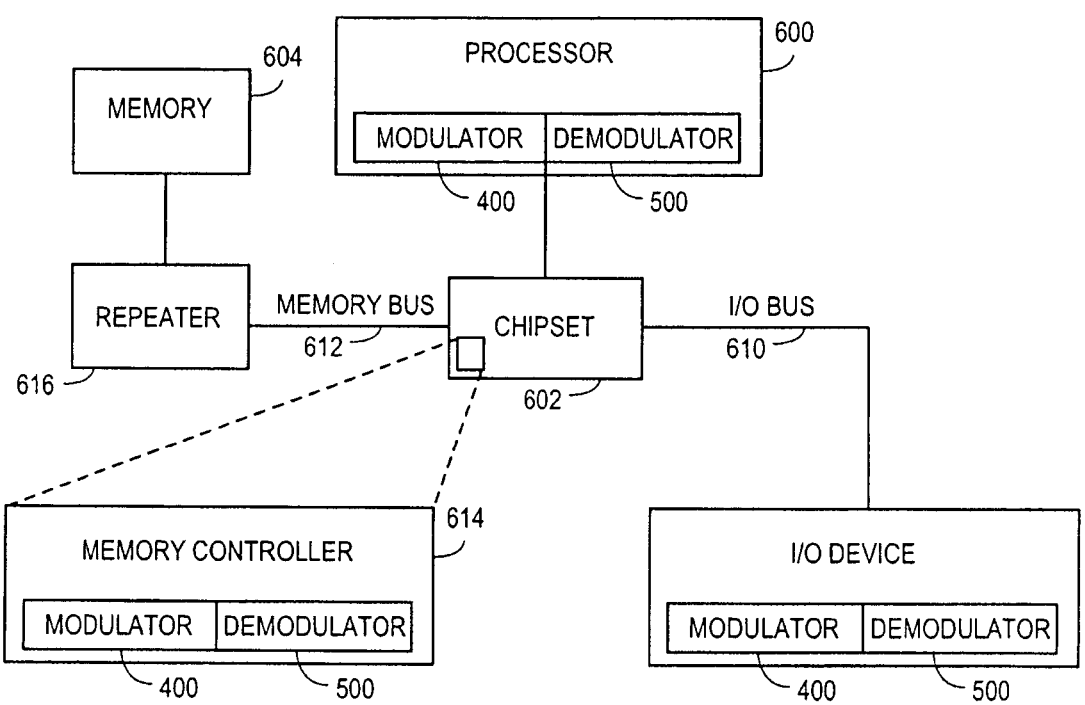
FIG. 7 is a block diagram of the system incorporating one embodiment of the invention.

FIG. 7 is a block diagram of the system incorporating one embodiment of the invention. The processor 600 includes a modulator 400 and demodulator 500. The processor 600 is coupled to a chipset 602 (which also contains the same modulators and demodulators), which is coupled to a memory bus 612 and an I/O bus 610. The chip set includes a memory controller 614, which also includes a modulator 400 and a demodulator 500. The improved modulation efficiency provided by modulator 400 and demodulator 500 ameliorates bandwidth bottlenecks between the processor 600 and memory subsystems. It may similarly relieve bottleneck between chip set 602 and I/O devices.

The memory controller interacts with the memory 604 over memory bus 612 via repeater 616. In one embodiment, repeater 616 is a low latency regenerative repeater. Using the above-described modulation scheme, since amplitude transitions occur in known FTU time slots, they may be regenerated with a minimum regeneration processing delay. Conversely, if an asynchronous modulation scheme were used complete demodulation and remodulation would be required to regenerate the symbols. Such low latency regenerative repeaters 616 may be used where signals travel long distances or, for example, in point-to-point connected buffered dynamic inline memory modules (DIMMs) in a memory subsystem where pin count and cost on the memory controller require cascade rather than replicate busses. "Long" as used in this context is when the channel loss would cause the BER to exceed the specification without regeneration.

An I/O device 606, which also contains a modulator 400 and a demodulator 500, is coupled to I/O bus 610 and may receive symbols modulated as previously described such that positions of modulation objects may overlap between symbol of the symbol set. The I/O device may include, for example, a disk controller.

In another embodiment, the memory controller is embedded in the processor. Such an embodiment may or may not have a chip set, but in any event, the memory interface would need to have the corresponding modulator/demodulator to gain a benefit of the described modulation technique during memory accesses.

In the foregoing specification, the invention has been described with reference to specific embodiments thereof. It will, however, be evident that various modifications and changes can be made thereto without departing from the broader spirit and scope of the invention as set forth in the appended claims. The specification and drawings are, accordingly, to be regarded in an illustrative rather than a restrictive sense.

The invention claimed is:

1. An apparatus comprising:
    a slot in edge group detector to determine if a transition occurred during an edge group having a plurality of fundamental time units (FTU's);
    demapping logic to extract data from the occurrence of the transition within an FTU of the edge group; and
    an amplitude (AM) demodulator coupled to the demapping logic, to identify data encoded in an amplitude level.

2. The apparatus of claim 1 further comprising:
    an edge detector to generate phase slot sized pulses responsive to an incoming signal.

3. The apparatus of claim 1 wherein the demapping logic comprises:
    an edge group to symbol converter; and
    a symbol to data converter.

4. The apparatus of claim 1 further comprising:
    a form synchronization unit to synchronize an output of the AM demodulator and the demapping logic.

5. The apparatus of claim 1 further comprising:
    a clock diskew unit to center a phase demodulation eye and an amplitude demodulation eye at a center of an FTU.

6. A method comprising:
    modulating with a modulator, data using symbols having a symbol period defined as an integer multiple of a fundamental time units (FTU), the symbol having modulation objects that are integer multiples of the FTU; and
    demodulating with a demodulator, the symbols to recover the data.

7. The method of claim 6 further comprising:
    providing a forwarded clock to receive with the symbols.

8. The method of claim 6 wherein demodulating comprises:
    recovering an embedded clock from a data stream including the symbols.

9. The method of claim 6 further comprising:
    regenerating the symbols between the modulating and demodulating without demodulating the symbols; and
    repeating the symbols over a communication channel.

10. The method of claim 6 wherein modulating comprises:
    encoding a fractional bit between a plurality of modulations; and
    wherein demodulating comprises recovering the bit by decoding the encoded fraction at a plurality of demodulators.

11. A system comprising:

a modulator to encode data in symbols having a symbol period that is an integer multiple of a fundamental time unit (FTU), each symbol having amplitude transition components that occur on an FTU time slot;

forwarded clock logic to mimic a delay through the modulator; and a demodulator coupled to the modulator and forwarded clock logic to decode the data from the symbols.

12. The system of claim 11 further comprising at least a second modulator and demodulator wherein at least one data bit is fractionally encoded across a plurality of modulators and decoded by a plurality of demodulators.

13. The system of claim 11 further comprising:

a regenerative repeater coupled between the modulator and the demodulator, the regenerative repeater to regenerate the symbols without demodulating the symbols.

* * * * *